United States Patent [19]

Rao et al.

[11] Patent Number: 4,843,002
[45] Date of Patent: Jun. 27, 1989

[54] METHOD OF SELECTING RECOMBINANT DNA-CONTAINING STREPTOMYCES

[75] Inventors: R. Nagaraja Rao, Indianapolis; Richard K. Stanzak, Poland, both of Ind.

[73] Assignee: Eli Lilly and Company, Indianapolis, Ind.

[21] Appl. No.: 655,180

[22] Filed: Sep. 27, 1984

[51] Int. Cl.$^4$ .................. C12N 15/00; C12N 1/20; C12P 21/00
[52] U.S. Cl. ..................... 435/172.3; 435/68; 435/252.3; 435/320; 435/872; 435/886; 435/889; 435/896; 435/252.35
[58] Field of Search ............... 435/172.3, 320, 80, 435/253; 935/14, 27, 75

[56] References Cited

U.S. PATENT DOCUMENTS 4,559,302 12/1985 Ingolia .................. 435/172.3

FOREIGN PATENT DOCUMENTS 2100738 1/1983 United Kingdom ............ 435/172.3

OTHER PUBLICATIONS

Bibb, M. J., K. F. Chater and D. A. Hopwood, In: M. Inouye, ed. *Experimental Manipulation of Gene Expression*, Academic Press, N.Y., 1983, pp. 53–82.
K. R. Kaster, S. G. Burgett, R. N. Rao and T. D. Ingolia, *Nucleic Acids Research*, 11(19), 6895–6911.
Kuhstoss, S and R. N. Rao, *Gene* 26: 295–299, 1983.
Santerre, R. F., N. E. Allen, J. N. Hobbs, R. N. Rao, and R. J. Schmidt, *Gene* 30: 147–156, 1984.
Manis et al., Abstracts of the *Annual Meeting of the American Society for Microbiology*, 1984, H170.
Collins et al., *Proc. Natl. Acad. Sci. USA* 75(9), 4242–46, 1978, Bates et al., *Gene* 26: 137–146, 1983.
Tandeau de Marsae et al., *Gene* 20: 111–119, 1982.
Frey et al., *Gene* 24: 299–308, 1983.
Lechevalier et al., *Heptaene Macrolide Antibiotics* XI: 640–647, 1961.
Mishra et al., *J. Clinical Micro* 11(6), 728–736, 1980.
Rao et al., *Antimicrob Agents Chemother* 24(5); 689–695, 1983.
Maniatis et al., *Molecular Cloning*, Cold Spring Harbor Laboratory, 1982, p. 5.
Davies and O'Connor, 1978, Antimicrobial Agents and Chemotherapy 14(1):69.
Davies and Jimenez, 1980, American Journal of Tropical Medicine and Hygiene 29(5) Supp: 1089.
Hedges and Shannon, 1984, Journal of General Microbiology 130:473.
Beneniste and Davies, 1973, Proceedings of the National Academy of Sciences, USA 70(8): 2276.
Bräu et al., 1984, Molecular and General Genetics 193:179.
Thompson et al., 1982, Gene, 20:51.
Schottel et al., 1981, Journal of Bacteriology, 146:360.
Thompson et al., 1980, Nature 286:525.

Primary Examiner—T. G. Wiseman
Assistant Examiner—Thomas D. Mays
Attorney, Agent, or Firm—Gerald V. Dahling; Leroy Whitaker

[57] ABSTRACT

A novel method of selecting Streptomyces recombinant DNA-containing host cells and vectors useful in exemplifying the method are described. The vectors confer apramycin resistance to sensitive Streptomyces host cells and thus provide a convenient method of selecting Streptomyces transformants. The apramycin resistance-conferring gene used in the method is an acetyltransferase aac(3)IV gene and can be isolated from *E. coli* K12 BE1041/pKC309 (NRRL B-15827) on an ~1.5 kb PstI-EcoRI restriction fragment.

38 Claims, 6 Drawing Sheets

Restriction Site and Function Map of
Plasmid pKC309
(6821bp)

Restriction Site and Function Map of
Plasmid pKC326
(9721bp)

Restriction Site and Function Map of
Plasmid pKC345
(10771bp)

Restriction Site and Function Map of
Plasmid pKC355
(9721bp)

Restriction Site and Function Map of
Plasmid pKC309
(6821bp)

Restriction Site and Function Map of
Cosmid pKC420
(10657bp)

Restriction Site and Function Map of
Phage pKC3310
(39744bp)

METHOD OF SELECTING RECOMBINANT DNA-CONTAINING STREPTOMYCES

SUMMARY OF THE INVENTION

The present invention is a method for selecting a recombinant DNA-containing *Streptomyces* host cell. The invention further comprises recombinant DNA cloning vectors and transformants useful in executing the method.

The present method requires, and the inventors provide, apramycin resistance-conferring cloning vectors for use in *Streptomyces*. The development and exploitation of recombinant DNA technology in *Streptomyces* is dependent upon the availability of selectable genetic markers on suitable cloning vectors. This development has been somewhat retarded by the low number of selectable markers presently available for use in *Streptomyces*. The present invention is useful and especially important in that it expands the number of selectable markers suitable for such use.

The vectors of the present method are particularly useful because they are small, versatile and can be transformed and selected in any *Streptomyces* cell that is sensitive to apramycin. *Streptomyces* provides over half of the clinically important antibiotics and thus is a commercially significant group. The present invention provides new and useful cloning systems and vectors for this industrially important group and allows for the cloning of genes both for increasing the yields of known antibiotics, as well as for the production of new antibiotics and antibiotic derivatives.

The present invention further provides a method of selecting *Streptomyces* transformants from a background of untransformed cells. The method allows one to add non-selectable DNA to the present vectors, transform *Streptomyces* with the modified vectors and select apramycin-resistant transformants containing this otherwise non-selectable DNA. Since transformation is a very low frequency event, such a functional test is a practical necessity for determining which cell(s), of among the millions of cells, has acquired the transforming DNA.

For purposes of the present invention, as disclosed and claimed herein, the following terms are defined below.

Recombinant DNA Cloning Vector—any autonomously replicating or integrating agent, including, but not limited to, plasmids, comprising a DNA molecule to which one or more additional DNA segments can be or have been added.

Transformation—the introduction of DNA into a recipient host cell that changes the genotype and, consequently, results in a change in the recipient cell.

Transformant—a recipient host cell that has undergone transformation.

Sensitive Host Cell—a host cell that cannot grow in the presence of a given antibiotic without a DNA segment that provides resistance thereto.

Transfectant—a recipient host cell that has undergone transformation by phage DNA.

Restriction Fragment—any linear DNA molecule generated by the action of one or more restriction enzymes.

Cosmid—a plasmid in which a phage cohesive end sequence is present, allowing in vivo or in vitro packaging of the plasmid DNA into infective particles.

Insertional Isomer—one of the two or more possible recombinant DNA molecules formed when a DNA segment is inserted at one of two or more compatible sites on the recipient DNA.

Phasmid—a recombinant DNA vector that may act as a phage or as a plasmid.

$Ap^R$—the ampicillin-resistant phenotype
$tsr^R$—the thiostrepton-resistant phenotype
$Am^R$—the apramycin-resistant phenotype
$Tc^R$—the tetracycline-resistant phenotype

DETAILED DESCRIPTION OF THE INVENTION

The present invention is a method for selecting a recombinant DNA-containing *Streptomyces* host cell, said method comprising:

(1) transforming an apramycin-sensitive, restrictionless *Streptomyces* host cell with a recombinant DNA cloning vector capable of autonomous replication or integration in said *Streptomyces* host cell, said vector comprising a DNA sequence that confers resistance to apramycin, and (2) culturing said transformed cell under conditions suitable for selection for apramycin resistance, subject to the limitation that said host cell is susceptible to transformation, cell division and culture. The present invention further comprises the vectors and transformants used to practice the aforementioned method.

The present method for selecting *Streptomyces* transformants by their expression of apramycin resistance is best illustrated by constructing vectors for transformation of assorted *Streptomyces* host cells. This is done by ligating the ~2.9 kilobase (kb) BamHI origin of replication-containing restriction fragment of pEL103 to BclI-digested plasmid pKC309. The resultant plasmid, designated as pKC326, is illustrative of the type of vector that is useful in the present method. A restriction site and function map of plasmid pKC326 is presented in FIG. 1 of the accompanying drawings.

Useful derivatives of plasmid pKC326 have also been constructed. One such derivative was made by ligating the ~1 kb BclI thiostrepton resistance gene containing restriction fragment of plasmid pIJ702 to BamHI-digested plasmid pKC326. The resultant plasmid, designated as pKC345, is useful for purposes of the present invention. Another derivative vector was constructed by digesting plasmid pKC309 was EcoRi, treating with the Klenow fragment of DNA Polymerase I and ligating the resulting fragment to the ~2.9 kb BamHI *Streptomyces* replicon-containing restriction fragment of plasmid pEL103. Those skilled in the art will recognize that the latter fragment must also be treated with Klenow fragment in order to carry out the above ligation. The resultant plasmid, designated as pKC355, further exemplifies the present invention. Restriction site and function maps of plasmids pKC345 and pKC355 are respectively presented in FIGS. 2 and 3 of the accompanying drawings.

The starting materials used in the construction of the above-mentioned vectors have been deposited and made part of the permanent stock culture collection of the Northern Regional Research Laboratory, Agricultural Research Service, 1815 North University Street, U.S. Department of Agriculture, Peoria, IL 61604 or the American Type Culture Collection, 12301 Parklawn Drive, Rockville, MD 20852. The accession numbers of the strains harboring the starting materials used in the above constructions are: (1) NRRL 12549-*Streptomyces granuloruber* No. A39912.13/pEL103; (2)

ATCC 39155-Streptomyces lividans/pIJ702; and (3) NRRL B-15827-*E. coli* K12 BE1041/pKC309. A restriction site and function map of plasmid pKC309 is presented in FIG. 4 of the accompanying drawings.

The present invention can also be exemplified by use of cosmid cloning vectors, such as, for example, cosmid pKC420. The latter vector has been deposited directly with the aforementioned Northern Regional Research Laboratory in *E. coli* K12 DH1/pKC420 and has been accorded the accession number NRRL B-15837. A restriction site and function map of cosmid pKC420 is presented in FIG. 5 of the accompanying drawings.

The above-illustrated vectors confer apramycin resistance to *Streptomyces* because of the presence of a functional acetyltransferase AAC(3)IV gene. Although the particular acetyltransferase gene accompanying the above vectors is identical to the G418 resistance gene disclosed in U.S. Patent Application Ser. No. 538,051, filing date 8-2-82, other known acetyltransferase AAC(-3)IV genes can be substituted. Such genes include, but are not limited to, those disclosed by Bräu et al., 1984, Molecular and General Genetics 193:179 and by Hedges and Shannon, 1984, Journal of General Microbiology, 130:473. In addition, a variety of different plasmid pKC309 restriction fragments that contain the apramycin resistance-conferring gene can also be substituted. The acetyltransferase AAC(3)IV gene is encoded on the ~1.5 kb PstI-EcoRI fragment of plasmid pKC309, therefore any restriction fragment containing the aforementioned ~1.5 kb PstI-EcoRI fragment also confers the desired resistance to sensitive *Streptomyces* host cells. Skilled artisans will recognize that all the above genes and fragments are functionally equivalent and thus can be used and interchanged for purposes of the present invention.

Restriction fragments used to construct vectors illustrative of the present invention can be conventionally modified to facilitate ligation. For example, molecular linkers can be provided to a particular acetyltransferase AAC(3)IV-containing restriction fragment or to DNA comprising the replication or integration functions of the vector. Thus, specific sites for subsequent ligation can be constructed conveniently. In addition, the acetyltransferase AAC(3)IV gene, origin of replication or integration sequences can be modified by adding, eliminating or substituting certain nucleotides to alter characteristics and to provide a variety of restriction sites for ligation of DNA. Those skilled in the art understand nucleotide chemistry and the genetic code and thus which nucleotides are interchangeable and which DNA modifications are desirable for a specific purpose. It is also noteworthy that the acetyltransferase AAC(3)IV gene is not limited to a particular position on a cloning vector, as long as the critical vector-controlled functions are not disrupted. Those skilled in the art understand or can readily determine which sites on a vector are advantageous for the ligation or insertion of a particular acetyltransferase gene-containing restriction fragment.

Although the above-described vectors comprise the *Streptomyces* replicon derived from plasmid pEL103, a variety of known *Streptomyces* replicons can be used to construct similar vectors. Table 1 is an illustrative, but not comprehensive, listing of *Streptomyces* plasmids from which additional functional *Streptomyces* replicons can be obtained. Those skilled in the art recognize that all or part of the plasmids may be used to construct vectors exemplifying the present invention so long as the replicon function is not disrupted. The plasmid-containing host and depository accession number are also listed in Table 1.

TABLE 1

| Streptomyces Plasmids | | |
|---|---|---|
| Plasmid | Host | Accession Number |
| SCP2 | *Streptomyces coelicolor* A3(2) | NRRL* 15042 |
| SCP2* | *Streptomyces coelicolor* M110 | NRRL 15041 |
| pEL7 | *Streptomyces ambofaciens* /pEL7 | NRRL 12523 |
| pUC6 | *Streptomyces espinosus* | NRRL 11439 |
| pUC3 | Streptomyces 3022A | NRRL 11441 |
| SLP1 | *Streptomyces lividans* | NCIB** 11417 |
| pNM100 | *Streptomyces virginiae* | NRRL 15156 |

*Agricultural Research Culture Collection (NRRL), 1815 North University Street, Peoria, Illinois 61604, United States of America
**National Collection of Industrial Bacteria (NCIB), Torry Research Station, Post Office Box 31, 135 Abbey Road, Aberdeen AB98DG, Scotland, United Kingdom Phage φC31 is a well-known *Streptomyces* phage that is an excellent source of starting material for constructing integrative, apramycin resistance-conferring vectors. A derivative of phage φC31, phasmid pKC331, is also useful for the purpose of constructing integrating vectors and can be obtained from *E. coli* K12 BE447/pKC331, a strain deposited and made part of the permanent stock culture collection of the aforementioned Northern Regional Research laboratory under the accession number NRRL B-15828. Ligation of the ~37 kb PstI restriction fragment of phasmid pKC331 to the ~2.25 kb apramycin resistance-conferring PstI restriction fragment of plasmid pKC309 results in the derivative phage pKC3310. Phage pKC3310 is an integrative vector which confers apramycin resistance to *Streptomyces* and thus further exemplifies the present invention. A restriction site and function map of phage pKC3310 is presented in FIG. 6 of the accompanying drawings.

The vectors of the present invention comprise a *Streptomyces* replicon and an apramycin resistance-conferring restriction fragment. Because amplification and manipulation of plasmids is done faster and more efficiently in *E. coli* than in *Streptomyces*, it is convenient to add DNA sequences that also allow the vectors to replicate in *E. coli*. Thus, the additions of functional replicon-containing and antibiotic resistance-conferring restriction fragments from *E. coli* plasmids such as, for example, pBR322, pACYC184, pBR325, pBR328 and the like are highly advantageous and add to the general utility of vectors exemplifying the present invention.

The vectors for use in the present method confer apramycin resistance to sensitive *Streptomyces* or related host cells. Although 10 μg/ml of apramycin is generally toxic to *Streptomyces*, vectors of the present invention confer resistance to levels of apramycin approaching 0.2 mg/ml. The preferred apramycin concentration for purposes of selection, however, is about 20–50 μg/ml, since apramycin resistance is affected by pH, osmolarity and complexity of the media. While all embodiments of the present invention are useful, some of the recombinant DNA cloning vectors and transformants are preferred. Accordingly, preferred vectors and transformants are listed in Table 2.

TABLE 2

| Preferred Vectors and Transformants | |
|---|---|
| Vector | Transformant |
| pKC326 | *Streptomyces lividans* |
| pKC326 | *Streptomyces ambofaciens* |

TABLE 2-continued

Preferred Vectors and Transformants

| Vector | Transformant |
|---|---|
| pKC328* | Streptomyces lividans |
| pKC328 | Streptomyces ambofaciens |
| pKC345 | Streptomyces lividans |
| pKC345 | Streptomyces ambofaciens |
| pKC355 | Streptomyces lividans |
| pKC355 | Streptomyces ambofaciens |
| pKC420 | Streptomyces lividans |
| pKC420 | Streptomyces ambofaciens |

*This plasmid is identical to pKC326, except for the orientation of the ~2.9 kb BamHi Streptomyces replicon-containing restriction fragment.

The method and recombinant DNA cloning vectors of the present invention are not limited for use in a single species or strain of *Streptomyces*. To the contrary, the method and the vectors are broadly applicable and can be used with apramycin-sensitive host cells of many *Streptomyces* taxa, particularly restrictionless strains of economically important taxa that produce antibiotics such as aminoglycoside, macrolide, β-lactam, polyether and glycopeptide antibiotics. Such restrictionless strains are readily selected and isolated from *Streptomyces* taxa by conventional procedures well known in the art (Lomovskaya et al., 1980, Microbiological Reviews 44:206). Host cells of restrictionless strains lack restriction enzymes and, therefore, do not cut or degrade plasmid DNA upon transformation. For purposes of the present application, host cells containing restriction enzymes that do not cut any of the restriction sites of the present vectors are also considered restrictionless.

Preferred host cells of restrictionless strains of apramycin-sensitive *Streptomyces* taxa that produce aminoglycoside antibiotics, and in which the present method is especially useful and the present vectors can be transformed, include restrictionless cells of, for example: *S. kanamyceticus* (kanamycins), *S. chrestomyceticus* (aminosidine), *S. griseoflavus* (antibiotic MA 1267), *S. microsporeus* (antibiotic SF-767), *S. ribosidificus* (antibiotic SF733), *S. flavopersicus* (spectinomycin), *S. spectabilis* (actinospectacin), *S. rimosus* forma *paromomycinus* (paromomycins, catenulin), *S. fradiae* var. *italicus* (aminosidine), *S. bluensis* var. *bluensis* (bluensomycin), *S. catenulae* (catenulin), *S. olivoreticuli* var. *cellulophilus* (destomycin A), *S. lavendulae* (neomycin), *S. albogriseolus* (neomycins), *S. albus* var. *metamycinus* (metamycin), *S. hygroscopicus* var. *sagamiensis* (spectinomycin), *S. bikiniensis* (streptomycin), *S. griseus* (streptomycin), *S. erythrochromogenes* var. *narutoensis* (streptomycin), *S. poolensis* (streptomycin), *S. galbus* (streptomycin), *S. rameus* (streptomycin), *S. olivaceus* (streptomycin), *S. mashuensis* (streptomycin), *S. hygroscopicus* var. *limoneus* (validamycins), *S. rimofaciens* (destomycins), *S. hygroscopicus* forma *glebosus* (glebomycin), *S. fradiae* (hybrimycins neomycins), *S. eurocidicus* (antibiotic A16316-C), *S. aquacanus* (N-methyl hygromycin B), *S. crystallinus* (hygromycin A), *S. noboritoensis* (hygromycin), *S. hygroscopicus* (hygromycins), *S. atrofaciens* (hygromycin), *S. kasugaspinus* (kasugamycins), *S. kasugaensis* (kasugamycins), *S. netropsis* (antibiotic LL-AM31), *S. lividus* (lividomycins), *S. hofuensis* (seldomycin complex) and *S. canus* (ribosyl paromamine).

Preferred host cells of restrictionless strains of apramycin-sensitive *Streptomyces* taxa that produce macrolide antibiotics, and in which the present method is especially useful, include restrictionless cells of, for example: *S. caelestis* (antibiotic M188), *S. platensis* (platenomycin), *S. rochei* var. *volubilis* (antibiotic T2636), *S. venezuelae* (methymycins), *S. griseofuscus* (bundlin), *S. narbonensis* (josamycin, narbomycin), *S. fungicidicus* (antibiotic NA-181), *S. griseofaciens* (antibiotic PA133A, B), *S. roseocitreus* (albocycline), *S. bruneogriseus* (albocycline), *S. roseochromogenes* (albocycline), *S. cinerochromogenes* (cineromycin B), *S. albus* (albomycetin), *S. felleus* (argomycin, picromycin), *S. rochei* (lankacidin, borrelidin), *S. violaceoniger* (lankacidin), *S. griseus* (borrelidin), *S. maizeus* (ingramycin), *S. albus* var. *coilmyceticus* (coleimycin), *S. mycarofaciens* (acetylleukomycin, espinomycin), *S. hygroscopicus* (turimycin, relomycin, maridomycin, tylosin, carbomycin), *S. griseospiralis* (relomycin), *S. lavendulae* (aldgamycin), *S. rimosus* (neutramycin), *S. deltae* (deltamycins), *S. fungicidicus* var. *espinomyceticus* (espinomycins), *S. furdicidicus* (mydecamycin), *S. ambofaciens* (spiramycin, foromacidin D), *S. eurocidicus* (methymycin), *S. griseolus* (griseomycin), *S. flavochromogenes* (amaromycin, shincomycins), *S. fimbriatus* (amaromycin), *S. fasciculus* (amaromycin), *S. erythreus* (erythromycins), *S. antibioticus* (oleandomycin), *S. olivochromogenes* (oleandomycin), *S. spinichromogenes* var. *suragaoensis* (kujimycins), *S. kitasatoensis* (leucomycin), *S. narbonensis* var. *josamyceticus* (leucomycin A3, josamycin), *S. albogriseolus* (mikonomycin), *S. bikiniensis* (chalcomycin), *S. cirratus* (cirramycin), *S. djakartensis* (niddamycin), *S. eurythermus* (angolamycin), *S. fradiae* (tylosin, lactenocin, macrocin), *S. goshikiensis* (bandamycin), *S. griseoflavus* (acumycin), *S. halstedii* (carbomycin), *S. tendae* (carbomycin), *S. macrosporeus* (carbomycin), *S. thermotolerans* (carbomycin) and *S. albireticuli* (carbomycin).

Preferred host cells of restrictionless strains of apramycin-sensitive *Streptomyces* taxa that produce β-lactam antibiotics, and in which the present method is especially useful and the present vectors can be transformed, include restrictionless cells of, for example: *S. lipmanii* (A16884, MM4550, MM13902), *S. clavuligerus* (A16886B, clavulanic acid), *S. lactamdurans* (cephamycin C), *S. griseus* (cephamycin A, B), *S. hygroscopicus* (deacetoxycephalosporin C), *S. wadayamensis* (WS-3442-D), *S. chartreusis* (SF 1623), *S. heteromorphus* and *S. panayensis* (C2081X); *S. cinnamonensis, S. fimbriatus, S. halstedii, S. rochei* and *S. viridochromogenes* (cephamycins A, B); *S. cattleya* (thienamycin); and *S. olivaceus, S. flavovirens, S. flavus, S. fulvoviridis, S. argenteolus* and *S. sioyaensis* (MM 4550 and MM 13902).

Preferred host cells of restrictionless strains of apramycin-sensitive *Streptomyces* taxa that produce polyether antibiotics, and in which the present method is especially useful and the present vectors can be transformed, include restrictionless cells of, for example: *S. albus* (A204, A28695A and B, salinomycin), *S. hygroscopicus* (A218, emericid, DE3936), A120A, A28695A and B, etheromycin, dianemycin), *S. griseus* (grisorixin), *S. conglobatus* (ionomycin), *S. eurocidicus* var. *asterocidicus* (laidlomycin), *S. lasaliensis* (lasalocid), *S. ribosidificus* (lonomycin), *S. cacaoi* var. *asoensis* (lysocellin), *S. cinnamonensis* (monensin), *S. aureofaciens* (narasin), *S. gallinarius* (RP 30504), *S. longwoodensis* (lysocellin), *S. flaveolus* (CP38936), *S. mutabilis* (S-11743a) and *S. violaceoniger* (nigericin).

Preferred host cells of restrictionless strains of apramycin-sensitive *Streptomyces* taxa or related genera such as, for example, *Nocardia* that produce glycopeptide antibiotics, and in which the present method is especially useful and the present vectors can be transformed, include restrictionless cells of, for example: *Nocardia orientalis* and *S. haranomachiensis* (vancomycin); *Nocardia candidus* (A-35512, avoparcin), *S. eburosporeus* (LL-AM 374), *S. virginiae* (A41030) and *S. toyocaensis* (A47934).

Preferred host cells of other apramycinsensitive *Streptomyces* restrictionless strains in which the present method is especially useful include restrictionless cells of, for example: *S. coelicolor, S. granuloruber, S. roseosporus, S. lividans, S. acrimycins, S. glaucescens, S. parvilin, S. pristinaespiralis, S. violaceoruber, S. vinaceus, S. espinosus, S. azureus, S. griseofuscus, S. fradiae, S. ambofaciens* and *S. toyocaensis.*

The method and recombinant DNA cloning vectors of the present invention have broad utility and help fill the need for suitable cloning vehicles for use in *Streptomyces* and related organisms. Moreover, the ability of the present vectors to confer apramycin resistance provides a functional means for selecting transformants. This is important because of the practical necessity for determining and selecting the particular cells that have acquired vector DNA.

Additional DNA segments, that lack functional tests for their presence, can also be inserted onto the present vectors, and then transformants containing the non-selectable DNA can be isolated by apramycin selection. Such non-selectable DNA segments can be inserted at any site, except within regions necessary for plasmid function and replication or within the acetyltransferase AAC(3)IV gene, and include, but are not limited to, genes that specify antibiotic modification enzymes and regulatory genes of all types.

More particularly, a non-selectable DNA segment that comprises a gene is inserted on a plasmid such as, for example, plasmid pKC345 at the central SalI restriction site of the thiostrepton resistance gene. Such an insertion inactivates the thiostrepton resistance gene and thus allows for the easy identification of transformants containing the recombinant plasmid. This is done by first selecting for apramycin resistance and, secondarily, identifying those apramycin-resistant transformants that are not resistant to thiostrepton. Therefore, the ability to select for apramycin resistance in *Streptomyces* and related cells allows for the efficient isolation of the extremely rare cells that contain the particular non-selectable DNA of interest.

The functional test for apramycin resistance, as described herein above, is also used to locate DNA segments that act as control elements and direct expression of an individual antibiotic resistance gene. Such segments, including, but not limited to, promoters, attenuators, repressors, inducers, ribosomal binding sites and the like, are used to control the expression of other genes in cells of Streptomyces and related organisms.

The apramycin resistance-conferring vectors of the present invention are also useful for insuring that linked DNA segments are stably maintained in host cells over many generations. These genes or DNA fragments, covalently linked to the apramycin resistance-conferring fragment and propagated in Streptomyces, are maintained by exposing the transformants to levels of apramycin that are toxic to non-transformed cells. Therefore, transformants that lose the vector, and consequently any covalently linked DNA, cannot grow and are eliminated from the culture. Thus, the vectors of the present invention can stabilize and maintain any DNA sequence of interest.

The method, cloning vectors and transformants of the present invention provide for the cloning of genes to improve yields of various products that are currently produced in Streptomyces and related cells. Examples of such products include, but are not limited to, Streptomycin, Tylosin, Cephalosporins, Actaplanin, Narasin, Monensin, Tobramycin, Erythromycin and the like. The present invention also provides selectable vectors that are useful for cloning, characterizing and reconstructing DNA sequences that code: for commercially important proteins such as, for example, human insulin, human proinsulin, glucagon, interferon and the like; for enzymatic functions in metabolic pathways leading to commercially important processes and compounds; or for control elements that improve gene expression. These desired DNA sequences also include, but are not limited to, DNA that codes for enzymes that catalyze synthesis of derivatized antibiotics such as, for example, Streptomycin, Cephalosporin, Tylosin, Actaplanin, Narasin, Monensin and Erythromycin derivatives, or for enzymes that mediate and increase bioproduction of antibiotics or other products. The capability for inserting and stabilizing such DNA segments thus allows for increasing the yield and availability of antibiotics that are produced by Streptomyces and related organisms.

Streptomyces can be cultured in a number of ways using any of several different media. Carbohydrate sources which are preferred in a culture medium include, for example, molasses, glucose, dextrin and glycerol. Nitrogen sources include, for example, soy flour, amino acid mixtures and peptones. Nutrient inorganic salts are also incorporated and include the customary salts capable of hielding sodium, potassium, ammonia, calcium, phosphate, chloride, sulfate and like ions. As is necessary for the growth and development of other microorganisms, essential trace elements are also added. Such trace elements are commonly supplied as impurities incidental to the addition of other constituents of the medium.

Streptomyces is grown under aerobic culture conditions over a relatively wide pH range of about 5 to 9 at temperatures ranging from about 15° to 40° C. For plasmid stability and maintenance, it is desirable to start with a culture medium at a pH of about 7.2 and maintain a culture temperature of abut 30° C.

The following examples further illustrate and detail the invention disclosed herein. Both an explanation of and the actual procedures for constructing the invention are described where appropriate.

EXAMPLE 1

Figure 1:
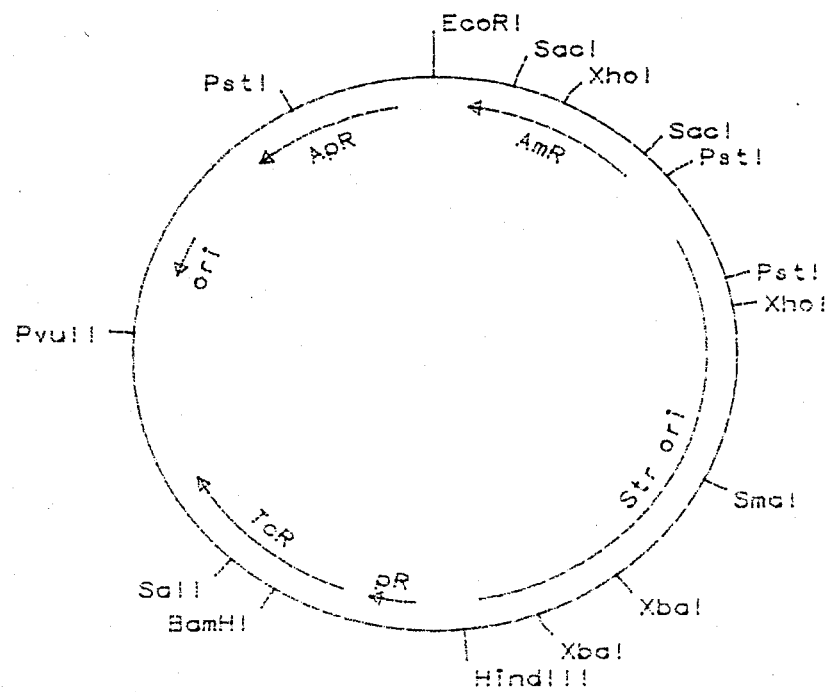
FIG. 1 shows the restriction site and function map of plasmid pKC326.
Figure 2:
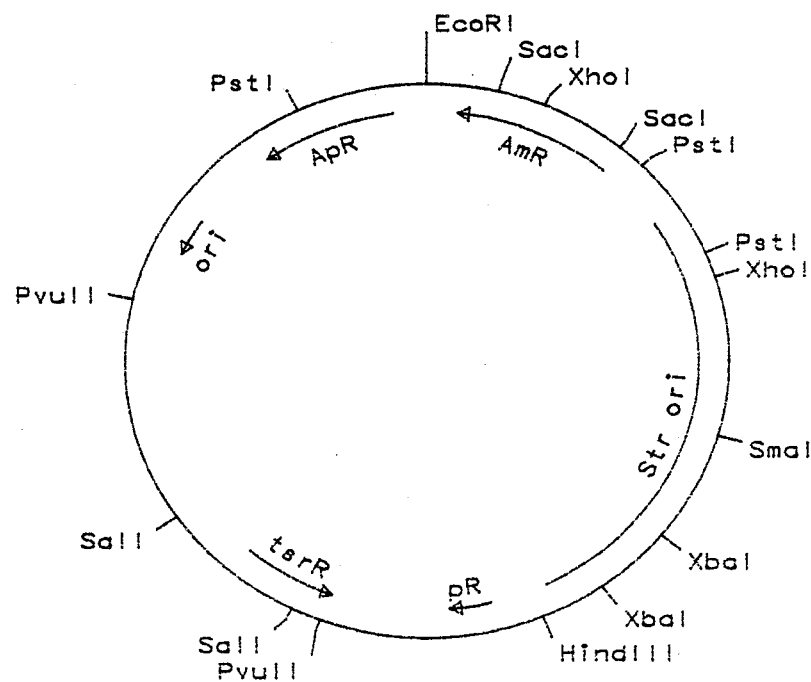
FIG. 2 shows the restriction site and function map of plasmid pKC345.
Figure 3:
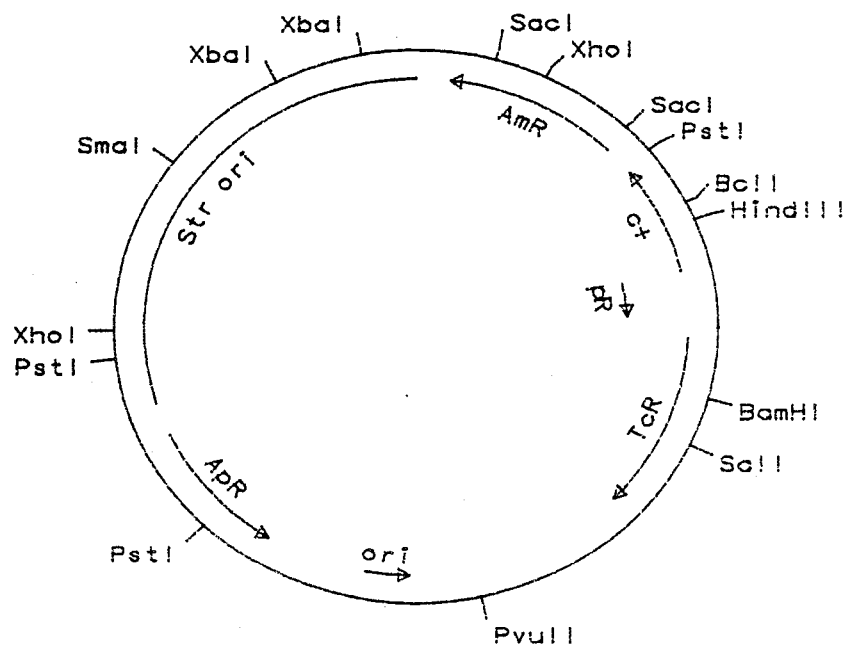
FIG. 3 shows the restriction site and function map of plasmid pKC355.
Figure 4:
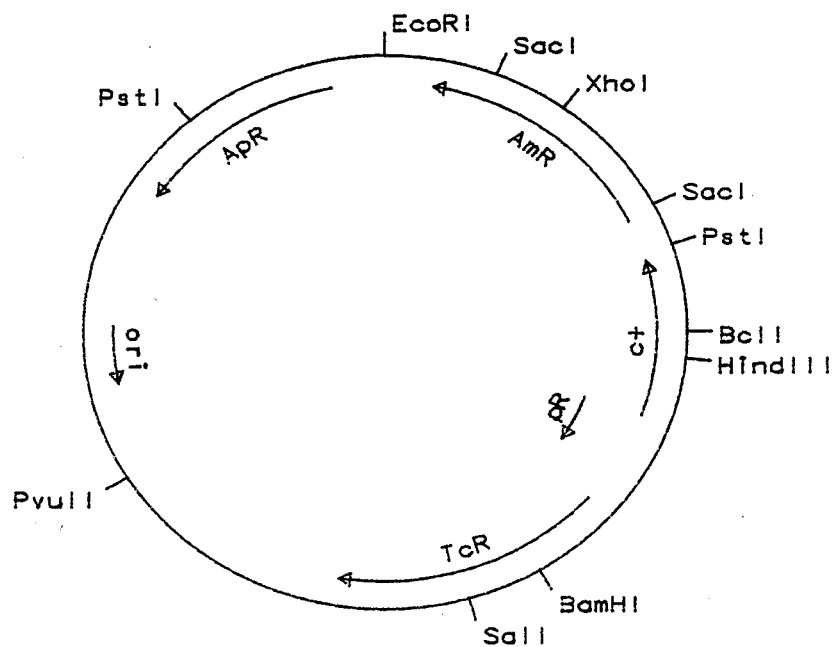
FIG. 4 shows the restriction site and function map of plasmid pKC309.

Culture of *E. coli* K12 BE1041/pKC309 and Isolation of Plasmid pKC309

A. Culture of *E. coli* K12 BE1041/pKC309

A 2 ml culture of *E. coli* K12 BE1041*/pKC309 (NRRL B-15827) was grown in the presence of 50 μg/ml ampicillin in TY media (1% tryptone, 0.5% NaCl and 0.5% yeast extract, pH 7.4) until the cells reached stationary phase.
*A strain deficient in adenine methylase, allowing one to digest the plasmid DNA with BclI The 2 ml culture was then used to inoculate a flask containing 1 liter of TY media containing 50 μg/ml ampicillin and growth was continued until the optical density at 550 nanometers was between 0.50 and 0.75. When the O.D. 550 reached the 0.50–0.75 range, 1 g of uridine was added, and, 15 minutes later, 170 mg of chloramphenicol was added. The incubation and culturing was then continued for 16 hours.

B. Isolation of Plasmid pKC309

The culture was centrifuged and the cell pellet resuspended in 10 ml of a solution that was 25% w/v sucrose; 50 mM Tris-HCl, pH 8; and 1 mM EDTA. Then, 2 ml of 0.5 M EDTA and 2 ml of a 5 mg/ml lysozyme solution in 0.25 M Tris-HCl, pH 8 were added to the resuspended cell pellet and the resultant mixture incubated at room temperature for 15 minutes. After the 15 minute incubation, 14 ml of a solution that was 50 mM Tris-HCl, pH 8; 6 mM EDTA; and 0.1% Triton X-100 were added to the lysozyme-treated cells and mixed by inversion.

The lysed cell mix was then centrifuged until the cell debris formed a loose pellet. The cell debris pellet was discarded and the supernatant extracted with buffered (pH 8) phenol. After phenol extraction, the aqueous phase was made 0.25 M in NaCl and two volumes of ethanol were added. After chilling the resultant mixture to −70° C., the nucleic acid was pelleted by centrifugation.

Further centrifugation (45,000 rpm, 16 hours, 20° C.) using cesium chloride gradients with ethidium bromide, was carried out to purify the plasmid DNA. Following centrifugation, the desired plasmid pKC309 DNA was collected and the ethidium bromide and cesium chloride removed by conventional procedures. The approximately 1 mg of plasmid pKC309 DNA obtained by this procedure was dissolved in 1 ml of TE buffer (10 mM Tris-HCl, pH 8 and 1 mM EDTA) and stored at −20° C.

EXAMPLE 2

Culture of Streptomyces granuloruber No. A39912.13/pEL103 and Isolation of Plasmid pEL103 DNA A. Culture of Streptomyces granuloruber No. A39912.13/ pEL103

A vegetative inoculum of *Streptomyces granuloruber* No. A39912.13/pEL103 (NRRL 12549) is conventionally prepared by growing the strain under submerged aerobic conditions in 50 ml of sterilized trypticase soy broth (TSB) at 30 g/l in deionized water (trypticase soy broth is obtained from Difco Laboratories, Detroit, Mich.

The trypticase soy broth inoculum is incubated for 48 hours at a temperature of 30° C. After incubation, about 10 ml of the inoculum are transferred to 500 ml of the sterilized broth and incubated for about 20 hours at 30° C. The pH is not adjusted. After incubation, the *Streptomyces granuloruber* No. A39912.13/pEL103 cells are ready for harvest and subsequent isolation of plasmid DNA.

B. Plasmid Isolation

About 12 g (wet wgt.) of *Streptomyces granuloruber* No. A39912.13/pEL103 cells are harvested by centrifugation (10 minutes, 4° C., 10,000 rpm). About 50 ml of TES buffer (0.01 M Tris(hydroxymethyl)amino-ethane [tris] 0.001 M EDTA and 34% sucrose, pH 8) were added to the cells followed by about 0.25 g of lysozyme in 10 ml of 0.25 M EDTA. After the mixture is incubated at 37° C. for about 15 minutes, about 0.1 ml of 10% Triton X-100 in TE buffer (0.01 M Tris and 0.001 M EDTA, pH 8) is added. The resultant mixture is then incubated at 65° C. for about 15 minutes. After the lysate is centrifuged (45 minutes, 4° C. and 18,000 rpm), the supernatant is extracted four times with buffered phenol and once with chloroform-isoamyl alcohol solution (24:1). Next about 0.5 ml of 3 M sodium acetate is added to the aqueous phase followed by 3 volumes of cold (−20° C.) 95% ethanol. The ethanol precipitation is rapidly performed in a dry ice-ethanol bath and the DNA precipitate is collected by centrifugation (15 minutes, 4° C. and 10,000 rpm). The precipitate is vacuum dried and then resuspended in 1.1 ml of STE buffer (0.1 M Tris, 0.001 M EDTA and 0.01 M sodium chloride). Centrifugation (40 hours, 15° C. and 35,000 rpm) using cesium chloride gradients, with ethidium bromide, is carried out to purify the plasmid DNA. Following centrifugation, the desired plasmid pEL103 DNA band is removed and the ethidium bromide extracted by conventional procedures. After precipitation of the DNA in 3 volumes of ethanol, the thus isolated plasmid pEL103 DNA is dissolved in 1 ml of 10 fold diluted TE buffer and is then frozen at −20° C. for storage.

EXAMPLE 3

Construction of Plasmid pKC326

A. BclI Digestion of Plasmid pKC309

Approximately 2 μg (2 μl) of plasmid pKC309 isolated in Example 1 were added to 2 μl of 10X BclI salts,* 1 μl (~5 Units) of restriction endonuclease BclI and 15 μl of H$_2$O and, after gentle mixing, reacted at 50° C. for one hour.
*The composition of 10X BclI salts is:
750 mM KCl
60 mM Tris-HCl pH 7.4
100 mM MgCl$_2$
10 mM dithiothreitol
1 mg/ml BSA After reacting, the digest was extracted once with buffered (pH 8) phenol and once with CHCl$_3$. The NaCl concentration was then adjusted to 0.25 M and two volumes of ethanol added. After mixing, the solution was chilled to −70° C. and the nucleic acid pelleted by centrifugation. The supernatant was discarded and the DNA pellet rinsed once with 70% ethanol and then dried. The BclI-digested plasmid pKC309 was then resuspended in 5 μl of H$_2$O.

B. Isolation of the ~2.9kb Replicon-Containing BamHI Fragment of Plasmid pEL103.

Approximately 50 μg (50 μl) of the plasmid pEL103 DNA isolated in Example 2 are added to 10 μl 10X BamHI salts,* 10 μl (~50 Units) of restriction endonuclease BamHI and 30 μl of H$_2$O and incubated at 37° C. for two hours. The digest is then extracted once with buffered phenol and then electrophoresed on a 1% agarose gel. The desired ~2.9kb BamHI fragment of plasmid pEL103 is then isolated by conventional electrophoretic gel means; about 5 μg of the fragment are obtained. The purified fragment is suspended in 10 μl of TE buffer.

*The composition of 10X BamHI salts is:
1.5 M NaCl
60 mM Tris-HCl, pH 7.9
60 mM MgCL₂
1 mg/ml BSA Ligation of BclI-Cut Plasmid pKC309 to the ~2.9 kb BamHI Restriction Fragment of Plasmid pEL103

All 5 μl of the BclI-cut plasmid pKC309 isolated in Example 3A were added to 2 μl of the ~2.9 kb BamHI fragment isolated in Example 3B, and then 3 μl of 10X T4 DNA ligase buffer,* 1 μl (~500 Units) of T4 DNA ligase and 19 μl of H₂O were added to the DNA. After gentle mixing, the reaction mixture was incubated at 16° C. for two hours. This reaction produced plasmid pKC326 along with another plasmid, pCK328, that differs from plasmid pKC326 only in the orientation of the ~2.9 kb BamHI fragment of plasmid pEL103.

*10X Ligase buffer is:
500 mM Tris-HCl, pH 7.8
100 mM MgCL₂
200 mM dithiothreitol
10 mM ATP
500 μg/ml BSA D. Isolation of Plasmids pKC326 and pKC328

The ligated DNA of Example 3C was used to transform E. coli according to the procedure of Maniatis et al., 1982, Molecular Cloning, Cold Spring Habor Laboratory, Cold Spring Harbor N.Y. The identity of the desired transformants was confirmed by restriction endonuclease digestion and subsequent gel analysis of the plasmid DNA isolated from the transformants. Those skilled in the art understand that the procedure given in Example 1 may be modified to omit the cesium chloride gradient step in order to speed the process of obtaining plasmid DNA for verification of structure. Once the plasmid structures were shown to be correct, large amounts of very pure plasmids pKC326 and pKC328 were obtained by substantial accordance with the method of Example 1.

EXAMPLE 4

Isolation of Plasmid pIJ702

*Streptomyces lividans*/pIJ702 may be obtained under the accession number ATCC 39155 from the American Type Culture Collection, 12301 Parklawn Drive, Rockville, MD 20852. This strain was cultured and the plasmid pIJ702 DNA purified in substantial accordance with the method of Example 2, using appropriate antibiotic selection. The plasmid pIJ702 DNA obtained was suspended in TE at a concentration of 1 μg/μl and stored at −20° C.

EXAMPLE 5

Construction of Plasmid pKC345

A. BamHI Digestion of Plasmid pKC326

Approximately 2 μg (2 μl) of plasmid pKC326 prepared in Example 3D were digested with 1 μl (~5 Units) of restriction endonuclease BamHI. After digestion, the reaction was treated in substantial accordance with the procedure of Example 3A, paragraph 2.

B. Isolation of the ~1 kb BclI Thiostrepton Resistance-Conferring Restriction Fragment of Plasmid pIJ102

Approximately 50 μg (50 μl) of plasmid pIJ702 were added to 10 μl 10X BclI salts, 10 μl restriction enzyme BclI (~50 Units) and 30 μl of H₂O and, after gentle mixing, reacted at 50° C. for 2 hours. The digest was then extracted once with buffered phenol and the desired ~1 kb BclI fragment isolated by conventional electrophoretic gel means. Approximately 5 μg of the desired fragment were obtained and suspended in 10 μl of TE buffer.

C. Ligation of BamHI-Cut Plasmid pKC326 to the ~1 kb BclI Thiostrepton Resistance-Conferring Restriction Fragment of Plasmid pIJ702

This ligation was carried out in substantial accordance with the ligation procedure of Example 3C, except that different restriction fragments were used. In this ligation, 5 μl of the BamHI-cut plasmid pKC326 prepared in Example 5A were ligated to 2 μl of the purified BclI restriction fragment prepared in Example 5B. This reaction produced plasmids pKC345 and pKC345A. Plasmid pKC345A differs from plasmid pKC345 only in the orientation of the ~1 kb BclI fragment of plasmid pIJ702.

D. Isolation of Plasmid pKC345

The ligated DNA of Example 5C was used to transform E. coli according to the procedure of Maniatis et al., 1982, Molecular Cloning, Cold Spring Harbor Laboratory, Cold Spring Harbor, N.Y. The identity of the desired transformants was confirmed by restriction endonuclease digestion and subsequent gel analysis of the plasmid DNA isolated from the transformants. Those skilled in the art understand that the procedure given in Example 1 may be modified to omit the cesium chloride gradient step in order to speed the process of obtaining plasmid DNA for verification of structure. Once the plasmid structure was shown to be correct, large amounts of very pure plasmid pKC345 were obtained by substantial accordance with the method of Example 1.

EXAMPLE 6

Construction of Plasmid pKC355

A. EcoRI Digestion of Plasmid pKC309

Approximately 2 μg (2 μl) of plasmid pKC309 were added to 2 μl 10X EcoRI* salts, 1 μl restriction enzyme EcoRI (~5 Units) and 15 μl H₂O and, after gentle mixing, reacted at 37° C. for 2 hours. After digestion, the reaction was treated in substantial accordance with the procedure of Example 3A, paragraph 2.

*The composition of 10X EcoRI salts is:
1.0 M Tris-HCl, pH 7.5
500 mM NaCl
50 mM MgCl₂
1 mg/ml BSA B. E. coli DNA Polymerase I - Large Fragment Treatment of EcoRI-Digested Plasmid pKC309

The 5 μl of EcoRI-cut plasmid pKC309 obtained in Example 6A were added to 5 μl of 10X *Ed. coli* DNA Polymerase I—Large Fragment buffer*; 5 μl of a solution that is 330 μM in each of dATP, dCTP, dGTP and TTP; 2 μl *E. coli* DNA Polymerase I—Large Fragment (~5 Units); and 33 μl of H₂O. After gentle mixing, the reaction was put at 37° C. for 30 minutes. After reaction, the DNA was treated in substantial accordance with the procedure of Example 3A, paragraph 2.

*The composition of 10X E. coli DNA Polymerase I—Large Fragment buffer is:
400 mM KPO₄, pH 7.5
10 mM 2-mercaptoethanol
66 mM MgCl₂

C. E. coli DNA Polymerase I—Large Fragment Treatment of the ~2.9 kb BamHI Streptomyces Replicon-Containing Restriction Fragment of pEL103

Approximately 2.5 μg (5.0 μl) of the purified fragment obtained in Example 3B were treated in substantial accordance with the procedure given in Example 6B.

D. Ligation of *E. coli* DNA Polymerase I—Large Fragment Treated Restriction Fragments The 5 μl of DNA obtained in Example 6B were ligated to the 5 μl of DNA obtained in Example 6C in substantial accordance with the teaching of Example 3C, except that the reaction was done at 4° C. for 16 hours as opposed to 16° C. for two hours. The longer ligation time at lower temperature was because blunt-ended fragments were involved in the ligation. This ligation reaction produced plasmids pKC355 and pKC355A. The two plasmids differ only in the orientation of the ~2.9 kb Streptomyces replicon.

E. Isolation of Plasmid pKC355

The ligated DNA of Example 5D was used to transform *E. coli* according to the procedure of Maniatis et al., 1982, Molecular Cloning, Cold Spring Harbor Laboratory, Cold Spring Harbor, N.Y. The identity of the desired transformants was confirmed by restriction endonuclease digestion and subsequent gel analysis of the plasmid DNA isolated from the transformants. Those skilled in the art understand that the procedure given in Example 1 may be modified to omit the cesium chloride gradient step in order to speed the process of obtaining plasmid DNA for verification of structure. Once the plasmid structure was shown to be correct, large amounts of very pure plasmid pKC355 were obtained by substantial accordance with the method of Example 1.

EXAMPLE 7

Isolation of Phasmid pKC331

The strain harboring phasmid pKC331 is *E. coli* K12 BE447 and may be obtained from the Northern Regional Research Laboratory, Agricultural Research Service, 1815 North University Street, U.S. Department of Agriculture, Peoria, ILL 61604, under the accession number NRRL B-15828. Substantial accordance with the method of Example 1 is used to prepare approximately 1 mg of the phasmid DNA. The phasmid pKC331 DNA is then suspended in TE at a concentration of 1 μg/μl.

EXAMPLE 8

Construction of Phage pKC3310

A. PstI Digestion of Phasmid pKC331 and Isolation of the ~37 kb PstI Restriction Fragment About 10 μg (10 μl) of phasmid pKC331 isolated in Example 7 are added to 10 μl 10X PstI salts*, 2 μl restriction enzyme PstI (~10 Units) and 78 μl H$_2$O. After gentle mixing, the digest is allowed to react 2 hours at 37° C. After digestion, the ~37kb PstI fragment containing the phage φC31 sequences is purified by conventional electrophoretic gel means. The purified fragment obtained (~5 μg) is suspended in 5 μl.
*The composition of 10X PstI salts is:
1 M NaCl
100 mM Tris-HCl, pH 7.5
100 mM MgCl$_2$
1 mg/ml BSA B. Isolation of the ~2.25 kb PstI Apramycin Resistance-Conferring Restriction Fragment of Plasmid pKC309

About 50 μl (50 μg) of plasmid pKC309 isolated in Example 1 are added to 10 μl 10X PstI salts, 10 μl restriction enzyme PstI (~50 Units) and 30 μl H$_2$O. After gentle mixing, the digest is incubated at 37° C. for two hours. Following the PstI digestion, the digest is extracted once with buffered phenol (pH 8) and the desired ~2.25 kb PstI restriction fragment isolated by conventional electrophoretic gel means. Approximately 5 μg of the desired fragment are obtained and suspended in 10 μl of TE buffer.

C. Ligation of the ~2.25 kb Apramycin ResistanceConferring PstI Restriction Fragment to the ~37 kb PstI Restriction Fragment of Phasmid pKC331

This ligation is carried out in substantial accordance with the method of Example 3C, except that different restriction fragments are used. In this ligation, 2.5 μl of the ~37 kb PstI restriction fragment prepared in Example 8A are ligated to 2 μl of the fragment obtained in Example 8C. The ligation produces DNA of the desired phages pKC3310 and phage pKC3311. Phage pKC3311 differs from phage pKC3310 only in respect to the orientation of the ~2.25 kb PstI fragment. The ligated DNA is used to transform Streptomyces to obtain infective phage particles. The phage particles are then used to prepare aparamycin-resistant Streptomyces via chromosomal integration of the vector.

EXAMPLE 9

Construction of Streptomyces ambofaciens/pKC326

About 1 μg of the DNA from Example 3D and 200 μl of protoplasts of Streptomyces ambofaciens, a strain deposited and made part of the permanent stock culture collection of the Northern Regional Research Laboratories, Peoria, Ill., from which it is available to the public under the accession number NRRL 2420, were mixed with 500 μl of 55% polyethylene glycol (Sigma) in P medium (Hopwood and Wright, 1978, Molecular and General Genetics 162:307), vortexed and then aliquots of 25 μl and 250 μl were plated onto R2YE* plates with 3 ml of R2YE top agar. The plates were incubated for 18 hours at 30° C. and then overlayed with 3 ml of R2YE top agar containing sufficient apramycin for a final concentration of 50 μg/ml. The plates were then incubated for an additional 3 days at 30° C. The resultant *S. ambofaciens*/pKC326 apramycin resistant colonies were isolated according to known procedures, cultured, and then conventionally identified by restriction enzyme and agarose gel electrophoretic analysis of the constitutive plasmids (Maniatis et al., 1982).
*R2YE medium was prepared with the following composition per liter:
Sucrose-103 g
2.5% K$_2$SO$_4$-ml
MgCl$_2$-10.1 g
Glucose-10 g
Casamino acids-0.1 g
Agar-22 g
Trace Element Mix-2 ml
0.5% KH$_2$PO$_4$-10 ml
1 M CaCl$_2$-20 ml
Proline-3 g
0.25 M TES pH 7.2-100 ml
50 ml 10% yeast extract Representative transformants constructed in accordance with the foregoing teachings include, but are not limited to, the following transformants listed in Table 3.

Table 3

Representative Transformants

1. Streptomyces R/R$^1$ wherein R is *ambofaciens, aureofaciens, griseofuscus, fradiae*, lividans, cinnamonensis* or *toyocaensis* and wherein R$^1$ independently is a plasmid from the group consisting of pKC326, pKC328, pKC345, pKC345A, pKC355, pKC355A or pKC420.
*The following procedure is used for transforming *S. fradiae*. Use low OD cells (less than 4 O.D. units) grown at 29° C. in the presence of 0.4% glycine in TSB medium. Protoplasts are formed in the presence of 1 mg/ml lysozyme in P medium on ice followed by two washes with P medium. Chill for 1-3 hours and then warm to ambient temperature.

Mix 0.8 μg calf thymus DNA and 1.5 μg protamine sulfate for one minute, then add: purified plasmid DNA (less than 100 ng) suspended in 10 μl of P medium, 200 μl of diluted protoplasts (⅓x), 0.9 ml of 55% PEG 1000 and mix for one minute. Using soft agar overlays, plate protoplasts and incubate at 29° C. for 16–24 hours then overlay with the appropriate antibiotic. Reincubate at 29° C. and score the plates in 7–10 days.

EXAMPLE 10

Construction of Streptomyces lividans/pKC3310

The ligated DNA of Example 8C, 200 μl of protoplasts of *Streptomyces lividans* (NRRL B-b 15828), $10^8$ spores of *Streptomyces lividans* and 500 μL of 55% polyethylene glycol in P medium are vortexed and aliquots of 25 μl and 250 μl are plated onto R2YE plates with 3 ml of R2YE top agar. The plates are incubated at 37° C. Plaques can usually be seen after ~20 hours. After plaques appear, they are removed from the plate and the phage particles washed off the agar into TSB medium. Serial dilutions of the phage suspension are made and aliquots removed and mixed with $10^8$ spores of *Streptomyces lividans*. These dilutions are made in order to achieve a good plaque distribution on the plate. The mixtures are plated on R2YE plates and incubated at 30° C. until sporulation occurs, a process taking about 4 days. After sporulation, the plates are replica plated onto fresh R2YE plates containing 50 μg/ml apramycin. The replica plates are then incubated at 30° C. for 3–4 days, and the resultant *S. lividans*/pKC3310 apramycin resistant colonies are isolated, cultured, and identified according to known procedures.

Representative transfectants constructed in accordance with the foregoing teaching of Example 10 include, but are not limited to, the following transfectants listed in Table 4.

TABLE 4
Representative Transfectants

1. Streptomyces R/$R^1$ wherein R is *ambofaciens, griseofuscus, fradiae*\* and *lividans* and wherein $R^1$ independently is a phage from the group consisting of pKC3310 and pKC3311.

\*The following procedure is used for transforming *S. fradiae*. Use low OD cells (less than 4 O.D. units) grown at 29° C. in the presence of 0.4% glycine in TSB medium. Protoplasts are formed in the presence of 1 mg/ml lysozyme in P medium on ice followed by two washes with P medium. Chill for 1–3 hours and then warm to ambient temperature.

Mix 0.8 μg calf thymus DNA and 1.5 μg protamine sulfate for one minute, then add less than 100 μg of phage DNA suspended in P medium, 200 μl of diluted protoplasts (⅓x), 0.9 ml of 55% PEG 1000 and $10^8$ spores of *S. fradiae* and mix for one minute. Plate and score colonies in accordance with the teaching of Example 10.

We claim:

1. A method for selecting a recombinant DNA-containing Streptomyces host cell, said method comprising:
   (a) transforming an apramycin-sensitive, restrictionless Streptomyces host cell with a recombinant DNA cloning vector capable of autonomous replication or integration in said Streptomyces host cell, said vector comprising the apramycin resistance-conferring gene of plasmid pKC309, and
   (b) culturing said transformed cell under conditions suitable for selection for apramycin resistance,
subject to the limitation that expression of apramycin resistance-conferring activity is controlled by the promoter of said apramycin resistance-conferring gene of plasmid pKC309 and that said host cell in susceptible to transformation, cell division and culture.

2. The method of claim 1 wherein the recombinant DNA cloning vector is a plasmid.

3. The method of claim 1 wherein the recombinant DNA cloning vector is a cosmid.

4. The method of claim 1 wherein the recombinant DNA cloning vector is a phage.

5. The method of claim 2 wherein the plasmid is selected from the group consisting of pKC326, pKC328, pKC345, pKC345A, pKC355 and pKC355A.

6. The method of claim 2 wherein the plasmid is pKC326.

7. The method of claim 2 wherein the plasmid is pKC328.

8. The method of claim 2 wherein the plasmid is pKC345.

9. The method of claim 2 wherein the plasmid is pKC355.

10. The method of claim 3 wherein the cosmid is pKC420.

11. The method of claim 4 wherein the phage is selected from the group consisting of pKC3310 and pKC3311.

12. The method of claim 1 wherein the transformed Streptomyces host cell is selected from the group consisting of *Streptomyces ambofaciens, Streptomyces aureofaciens, Streptomyces griseofuscus, Streptomyces fradiae, Streptomyces lividans, Streptomyces cinnamonensis* and *Streptomyces toyocaensis*.

13. The method of claim 12 wherein the transformed host cell is *Streptomyces ambofaciens*/pKC326.

14. The method of claim 12 wherein the transformed host cell is *Streptomyces ambofaciens*/pKC328.

15. The method of claim 12 wherein the transformed host cell is *Streptomyces ambofaciens*/pKC345.

16. The method of claim 12 wherein the transformed host cell is *Streptomyces ambofaciens*/pKC355.

17. The method of claim 12 wherein the transformed host cell is *Streptomyces ambofaciens*/pKC420.

18. The method of claim 12 wherein the transformed host cell is *Streptomyces lividans*/pKC326.

19. The method of claim 12 wherein the transformed host cell is *Streptomyces lividans*/pKC328.

20. The method of claim 12 wherein the transformed host cell is *Streptomyces lividans*/pKC345.

21. The method of claim 12 wherein the transformed host cell is *Streptomyces lividans*/pKC355.

22. The method of claim 12 wherein the transformed host cell is *Streptomyces lividans*/pKC420.

Figure 5:
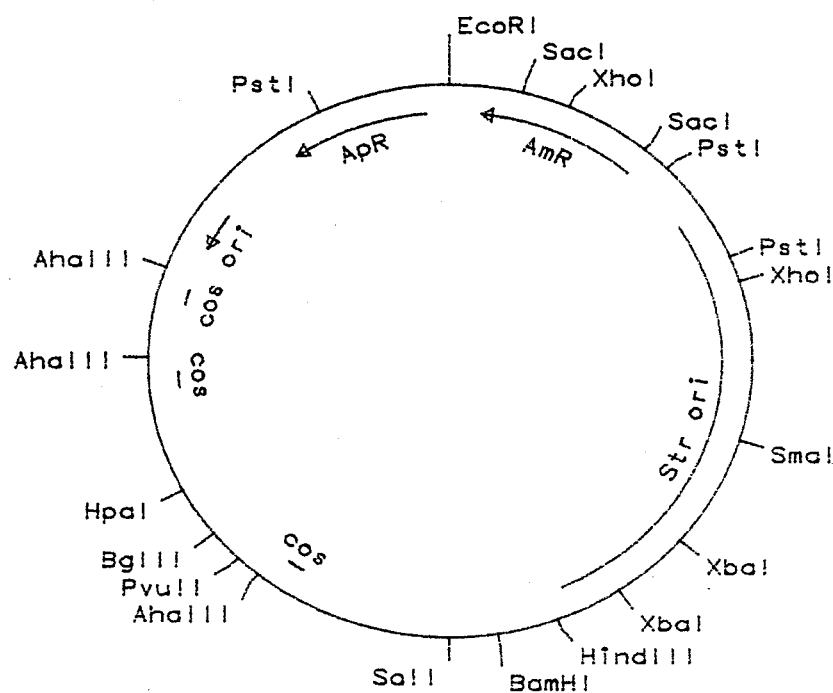
FIG. 5 shows the restriction site and function map of cosmid pKC420.
Figure 6:
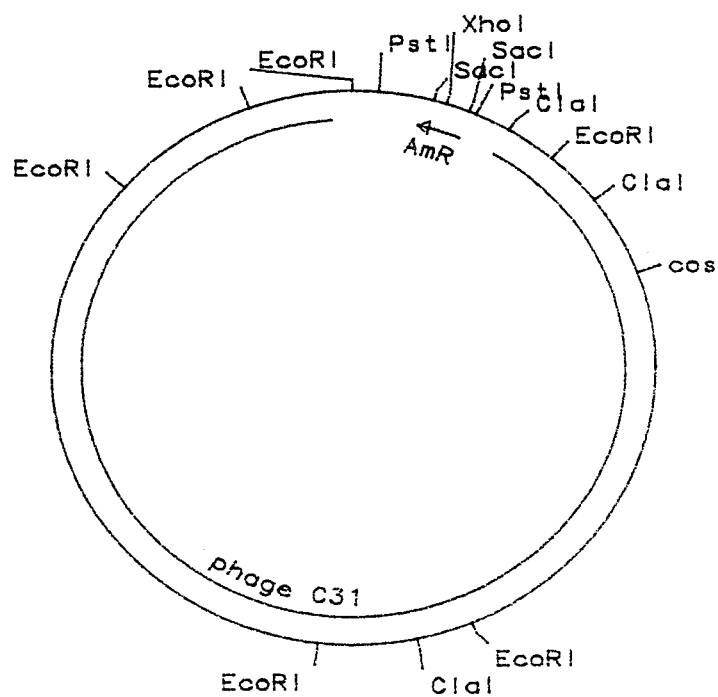
FIG. 6 shows the restriction site and function map of phage pKC3310.

23. A recombinant DNA vector capable of transforming an apramycin-sensitive restrictionless Streptomyces host cell and conferring apramycin resistance thereto, said vector comprising the apramycin resistance-conferring gene of plasmid pKC309, subject to the limitation that expression of apramycin resistance-conferring activity is controlled by the promoter of said apramycin resistance-conferring gene and subject to the further limitation that said vector does not comprise DNA having (1) the same order and relative position of restriction sites as depicted in the map of FIG. 5, or (2) the same linear order and relative position of restriction sites as would occur upon interrupting the map depicted in FIG. 5 at any single point.

24. A vector of claim 23 which is selected from the group consisting of plasmids pKC326, pKC328, pKC345, pKC345A, pKC355 and pKC355A; and of phages pKC3310 and pKC3311.

25. The vector of claim 24 that is plasmid pKC326.
26. The vector of claim 24 that is plasmid pKC328.
27. The vector of claim 24 that is plasmid pKC345.
28. The vector of claim 24 that is plasmid pKC355.
29. The vector of claim 24 that is phage pKC3310.
30. An apramycin-sensitive, restrictionless Streptomyces host cell transformed by a vector of claim 23.
31. The Streptomyces host cell of claim 30 transformed by a vector selected from the group consisting of plasmids pKC326, pKC328, pKC345, pKC345A, pKC355 and pKC355A; and of phage pKC3310 and pKC3311.
32. The transformed Streptomyces host cell of claim 31 that is *Streptomyces ambofaciens*.
33. The transformed Streptomyces host cell of claim 31 that is *Streptomyces lividans*.
34. The transformant of claim 32 that is *Streptomyces ambofaciens*/pKC345.
35. The transformant of claim 33 that is *Streptomyces lividans*/pKC3310.
36. A method for selecting a recombinant DNA-containing Nocardia host cell, said method comprising:
 (a) transforming an apramycin-sensitive, restrictionless Nocardia host cell with a recombinant DNA cloning vector capable of autonomous replication or integration in said Nocardia host cell, said vector comprising the apramycin resistance-conferring gene of plasmid pKC309, and
 (b) culturing said transformed cell under conditions suitable for selection for apramycin resistance,
subject to the limitation that expression of apramycin resistance-conferring activity is controlled by the promoter of said apramycin resistance-conferring gene of plasmid pKC309 and that said host cell is susceptible to transformation, cell division and culture.
37. The method of claim 36 wherein the recombinant DNA cloning vector is a plasmid.
38. An apramycin-sensitive, restrictionless Nocardia host cell transformed by a vector used in the method of claim 37.

* * * * *